United States Patent [19]

Williams

[11] Patent Number: 5,447,684
[45] Date of Patent: Sep. 5, 1995

[54] STERILIZATION DEVICES, SPORICIDAL COMPOSITIONS, STERILIZATION METHODS, AND DEVICES FOR REDUCING SURFACE TENSION

[76] Inventor: Robert M. Williams, 4568 Argyle Ter., NW., Washington, D.C. 20011

[21] Appl. No.: 162,312

[22] Filed: Dec. 6, 1993

Related U.S. Application Data

[63] Continuation-in-part of Ser. No. 991,093, Dec. 15, 1992, abandoned, which is a continuation-in-part of Ser. No. 434,851, Nov. 1, 1989, Pat. No. 5,171,523, which is a continuation-in-part of Ser. No. 252,522, Oct. 3, 1988, Pat. No. 5,041,264.

[51] Int. Cl.[6] .............................................. A61L 2/02
[52] U.S. Cl. ........................................ 422/20; 252/106; 252/354; 422/28; 422/33; 422/34; 422/35; 422/36; 422/37; 422/292
[58] Field of Search ............... 422/1, 20, 28, 33–37, 422/122, 128, 292, 294, 300; 252/106, 354

[56] References Cited

U.S. PATENT DOCUMENTS

| | | |
|---|---|---|
| 1,817,530 | 7/1927 | Spanel . |
| 3,282,775 | 11/1966 | Stonehill . |
| 3,708,263 | 1/1973 | Boucher . |
| 3,912,450 | 10/1975 | Boucher . |
| 4,093,744 | 6/1978 | Winicov et al. . |
| 4,224,367 | 9/1980 | Scholle . |
| 4,362,241 | 12/1982 | Williams . |
| 4,446,967 | 5/1984 | Halkyard . |
| 5,019,346 | 5/1991 | Richter et al. . |
| 5,208,257 | 5/1993 | Kabara . |
| 5,234,719 | 8/1993 | Richter et al. . |

*Primary Examiner*—Timothy M. McMahon
*Attorney, Agent, or Firm*—Beveridge, DeGrandi, Weilacher & Young

[57] ABSTRACT

Compositions, devices, and methods are disclosed for achieving rapid sterilization. A device for reducing surface tension in liquids is also disclosed. Both cationic and anionic surfactants are simultaneously present and used with a germicide to accelerate sterilization at room temperatures. One device includes a tablet, absorbent body, or other carrier which carries both an anionic surfactant and a cationic surfactant. Another device includes a hermetically sealable envelope which contains an anionic surfactant and a cationic surfactant, preferably with a germicide which impregnates an absorbent liner. The composition includes a germicide, an anionic surfactant, and a cationic surfactant. Glutaraldehyde solutions are the preferred germicides; sulfosuccinic acid, ester with ethoxylated lauryl alcohol, disodium salt is a preferred anionic surfactant; and, a quaternary ammonium salt is the preferred cationic surfactant. A sterilization method is performed by exposing an object to the disclosed compositions.

20 Claims, 2 Drawing Sheets

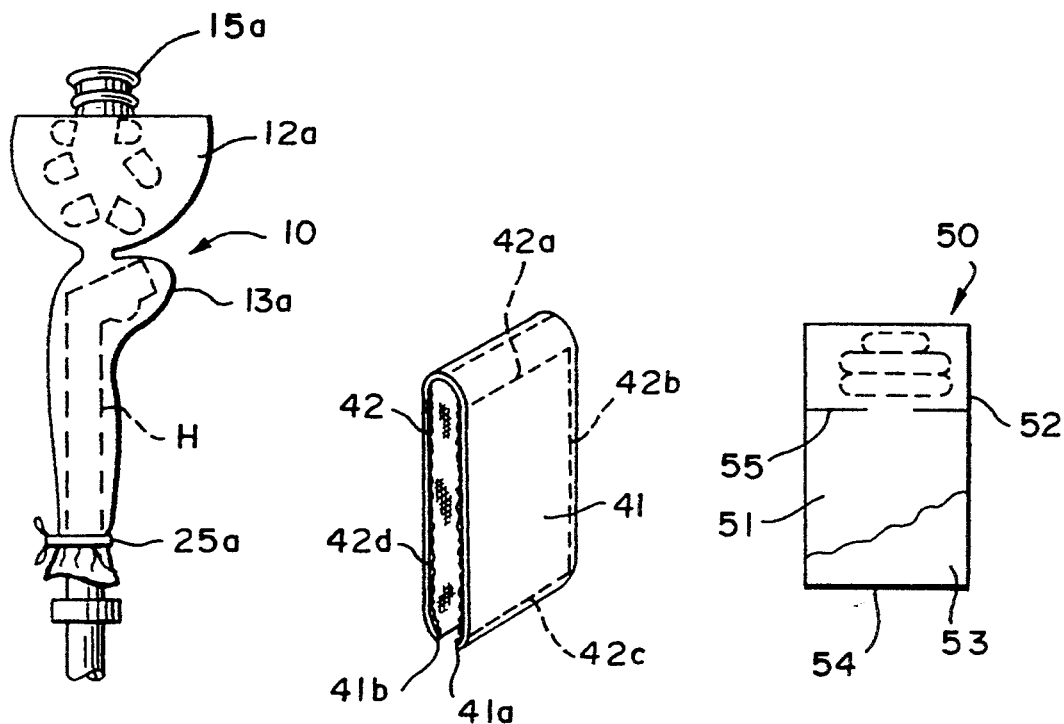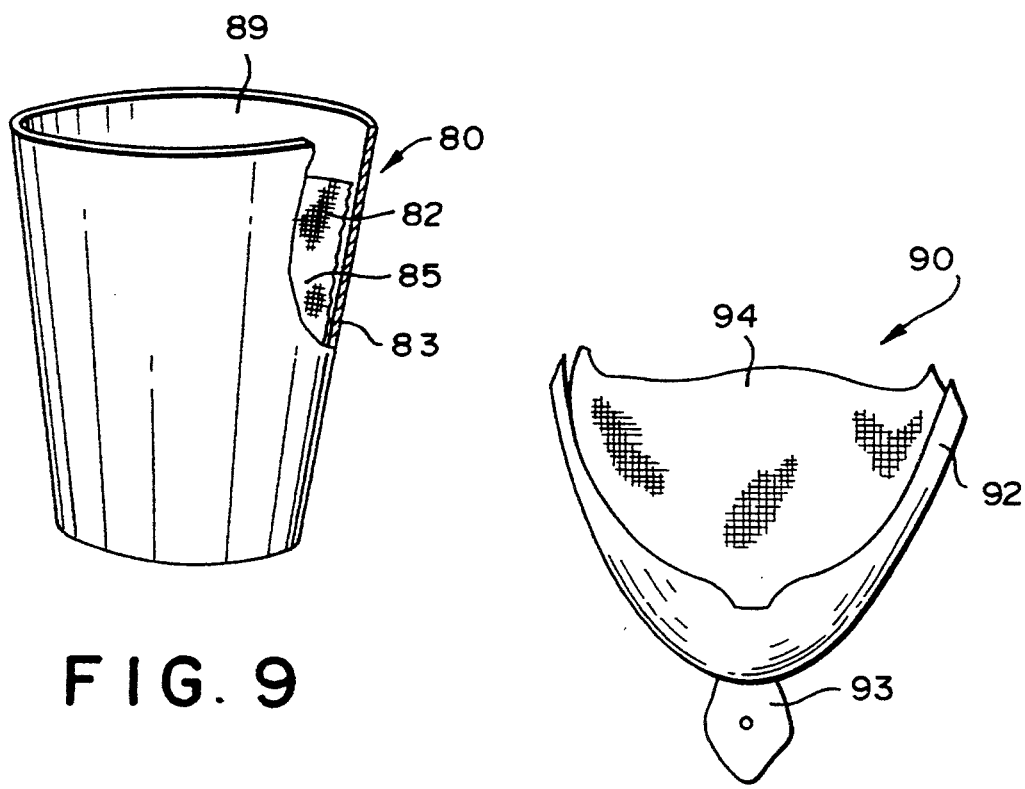

STERILIZATION DEVICES, SPORICIDAL COMPOSITIONS, STERILIZATION METHODS, AND DEVICES FOR REDUCING SURFACE TENSION

REFERENCE TO RELATED APPLICATIONS

This is a continuation-in-part of my U.S. patent application Ser. No. 07/991,093,filed Dec. 15, 1992, now abandoned, which, in turn, was a continuation-in-part of U.S. patent application Ser. No. 07/434,851, filed Nov. 1, 1989, now U.S. Pat. No. 5,171,523 which, in turn, was a continuation-in-part of my U.S. patent application Ser. No. 07/252,522, filed Oct. 3, 1988, now U.S. Pat. No. 5,041,264. The entire contents of these prior applications are incorporated herein by reference.

BACKGROUND OF THE INVENTION

Autoclaving, dry heat and chemical vapor sterilization methods have been accepted as most effective means for sterilizing inanimate objects such as medical and dental instruments and equipment used in patient treatment. Such methods, however, do have certain disadvantages. The processes are too tedious and cumbersome, and they require long contact times to achieve sterilization. Further, the sterilization process requires highly skilled personnel to operate and monitor the system. Many pieces of equipment, surgical instruments and material used in patient treatment are heat sensitive and too delicate to be exposed to sterilization methods requiring high temperatures. Additionally, some objects which require sterilization are not located at sites where the sterilization equipment is located.

There has been a considerable amount of research directed to finding alternative methods for sterilizing other than those requiring high temperatures. Many of the research efforts have pointed to sterilizing in liquid phase. A search of the scientific literature and the prior art has produced many examples directed to improving the aqueous sporicidal composition of germicides used to disinfect animate and inanimate surfaces and objects.

Glutaraldehyde in aqueous solution has received considerable attention aimed at increasing its potency and rapidity of sporicidal activity by the use of various combinations of active ingredients; or by increasing the temperature of the aqueous solution of glutaraldehyde enhanced by ultrasonic energy. To date, however, aqueous solutions of glutaraldehyde require from 6 ¾ hours to 10 hours contact time to destroy highly resistant spores such as *Bacillus subtilis* and *Clostridium sporogenes*. For this reason, aqueous solutions of glutaraldehyde are still relegated to a disinfecting role.

Liquid germicides hold out great promise as liquid sterilants if their antimicrobial properties can be accelerated to considerably shorten contact time for sporicidal action. The need for germicides in liquid phase having rapid and potent disinfecting and sterilizing compositions is highly desirable for inactivating microorganisms on inanimate and animate surfaces and objects. Germicides employed to disinfect and sterilize inanimate objects are termed "disinfectants"; those germicides employed to disinfect and sterilize animate surfaces are termed "antiseptics." Germicides should be able to penetrate into crevices, cavities, and beneath films of organic matter. Moreover, germicides should possess and maintain a strong lethal concentration in the presence of sputum, blood and fecal material. Germicides should have a wide antimicrobial spectrum; and importantly, germicides should achieve and maintain a low surface tension to enable effective and rapid absorption of the active ingredients at interface with a contaminated object.

Surfactants are extremely important in aqueous solution to lower surface tension. Without a surfactant, the antimicrobial activity of an aqueous solution is severely compromised. The efficacy of this invention is directed to the use of surfactants having opposing electrical charges, and which are generally considered to be incompatible when used together in aqueous solutions. Based on observations when these surfactants (anionic and cationic surface active agents) are exposed together experimentally, in aqueous solutions, they exhibit dramatic and outstanding properties in lowering surface tension not observed before. This invention is able to maintain and prevent the premature exposure and interaction of these surfactants to each other within a device, until the disinfecting process is initiated. When employing anionic and cationic surfactants in a 2% aqueous solution of acid glutaraldehyde, highly resistant spores are destroyed within 5–10 minutes, versus 6 ¾–10 hours in the conventional immersion system.

This invention makes use of a liquid absorbent material which contains, as dry constituents, anionic and cationic surfactants milled into said absorbent material at the manufacturing stage. When exposed to an aqueous solution, the surfactants are released from the liquid absorbent material to enhance significantly the surface active properties of said aqueous solution.

Aqueous solutions having cleaning, disinfecting, or sterilizing compositions, have their surface active properties greatly enhanced where anionic and cationic surfactants are employed. Because of their superior surface active activities when used together in aqueous solution, the need for long contact time necessary for antimicrobial activity is eliminated. A germicide like glutaraldehyde is elevated from a disinfectant to a liquid sterilant. A germicide, supplemented with anionic and cationic surfactants employed as an antiseptic, is able to reduce quickly the microorganism population residing on animate surfaces such as skin, mucosal membrane, and wound sites. The application of the invention is not limited to cleaning, disinfecting, and sterilizing purposes in the health field, but can be used to enhance aqueous solutions used as mouth washes, toothpastes and similar products to remove foreign material and bacteria from animate surfaces and inanimate objects.

It is accordingly one object of the present invention to present a device and method for storing anionic and cationic surfactants in a nonreactive state prior to use. It is accordingly another object of the present invention to present a potent sporicidal composition which can rapidly destroy highly resistant spores within minutes when practiced within the scope of the invention. It is another object of the present invention to demonstrate the strong enhancement of surface active properties achieved when employing the above surfactants in aqueous solutions. It is the further object of this invention to achieve rapid sporicidal activity, resulting in total destruction of highly resistant spores within minutes (5–10 minutes). And finally, in addition to the health field, it is another object of the present invention to apply the invention in a wide variety of applications such as in aqueous media of industrial and household products.

Referring now to the novelty and innovativeness of the invention, a search of the scientific literature and the prior art reveal no instance where anionic and cationic surfactants are employed together to lower surface tension in aqueous solution. For example, U.S. Pat. No. 3,282,775 (Stonehill) discloses the use of a cationic surfactant, only. U.S. Pat. No. 3,912,450 (Boucher) describes the use of anionic and nonionic surfactants together in aqueous solutions. U.S. Pat. No. 4,093,744 (Winicov) describes the use individually or severally nonionic, anionic and amphoteric surfactants.

SUMMARY OF THE INVENTION

The present invention relates to a device, composition including anionic and cationic surfactants, and method for the rapid cleaning, disinfecting and sterilizing in aqueous solutions of inanimate and animate surfaces and objects.

In one respect, the invention involves a device for enhancing the properties of solutions by reducing their surface tension. This device comprises a carrier, a cationic surfactant carried by the carrier, and an anionic surfactant carried by the carrier. These surfactants are releasable into solution when the carrier is brought into contact with a liquid, preferably a germicidal solution. The carrier may be a tablet, a porous body which has the surfactants in its interstices, a substrate which is coated by the surfactants, or other carriers.

In another respect, the invention involves a sterilization device which includes an envelope which is substantially impervious to gas and liquid, an anionic surfactant in the envelope, and a cationic surfactant in the envelope. The envelope has an internal chamber and a sealable opening which permits the insertion of an object into the chamber. Preferably, the envelope also has an internal liner, and the envelope contains a germicidal solution when in use. Glutaraldehyde germicidal solutions are preferred, but a wider range of germicidal solutions is possible including quaternary ammonium compounds, phenols, iodophores, chlorine compounds, alcohol compounds, and hydrogen peroxide. The liner itself may contain the cationic surfactant, and the glutaraldehyde solution may include the cationic surfactant so that the two surfactants are not brought together until the germicidal solution is introduced into the envelope. Alternatively, the anionic and cationic surfactants can be in the envelope, in non-reactive states relative to each other, before the germicidal solution is introduced into the envelope. The surfactants can also be in separate crushable capsules in the envelope, in an absorbent material in the envelope, or incorporated in the material which forms the envelope.

From another perspective, the invention involves a rapid sporicidal composition which comprises a germicide, an anionic surfactant, and a cationic surfactant. The surfactants can be contained in one or more porous bodies. Each surfactant may be present in a quantity of about 0.01 to 2% by weight of the composition, the cationic surfactant can be a quaternary ammonium salt; the anionic surfactant can be sulfosuccinic acid, ester with ethoxylated lauryl alcohol, disodium salt; and the germicide can be selected from the group consisting of quaternary ammonium compounds, phenols, iodophores, acidic potentiated glutaraldehydes, neutral glutaraldehydes, alkaline glutaraldehydes with buffer, chlorine compounds, alcohol compounds, and hydrogen peroxide. Preferably, the germicide is a solution containing about 0.01 to 2% by weight of a glutaraldehyde comprising a saturated dialdehyde having from 2 to 6 carbon atoms. Another solution can have a sufficient quantity of a lower alkanol to make a final alcohol concentration from about 60 to about 70%. A glutaraldehyde composition can include an alkaline salt providing the solution with a ph of about 7 to 8. Other glutaraldehyde solutions may have a ph of about 1 to 7.

The invention also includes a sterilizing method performed by exposing an object any of the sterilizing compositions of the invention. Preferably, the method is performed by providing an envelope which is substantially impervious to gas and liquid. The envelope may contain an anionic surfactant, and the germicidal solution introduced into the envelope may contain the cationic solution. Vacuum can be applied to remove air from the envelope, and the envelope can be subjected to ultrasonic waves.

The invention also involves a device for reducing the surface tension of liquid used for sterilization or for other purposes. Such a device involves a carrier, a cationic surfactant carried by the carrier, and an anionic surfactant carried by the carrier. The surfactants are releasable into solution when the carrier is brought into contact with the liquid. The carrier can be a tablet, a fabric or other porous body which has the surfactants in its interstices, a substrate which is coated by the surfactants, or a body into which the surfactants have been milled. The carrier may also include a liquid soluble germicide. The surfactants are preferably in a dry form, and the carrier may also include the dry form of a liquid soluble germicide.

BRIEF DESCRIPTION OF THE DRAWINGS

FIG. 6 is a side view of another embodiment of the present invention with an instrument in place.

FIG. 7 is a perspective view, partly in cross-section, of a further embodiment of the present invention.

FIG. 8 is a cross-sectional view of another embodiment of the invention.

FIG. 9 is a cross-sectional view of a rigid container and related components in accordance with the present invention.

FIG. 10 is an elevational view of another embodiment of the invention and related in accordance with the present invention.

DESCRIPTION OF THE PREFERRED EMBODIMENTS

Figure 1:
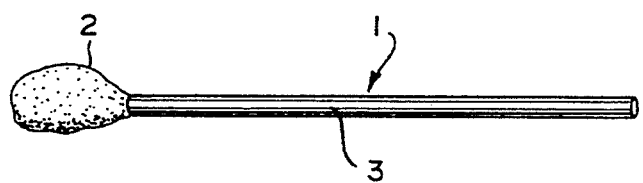
FIG. 1 is a side view of a swab applicator in accordance with the present invention.

Referring now to the drawings, wherein like or corresponding reference numerals are used to designate like or corresponding parts throughout the several views, there is shown in FIG. 1 a device 2 resembling a swab applicator. The device 2 comprises a liquid absorbent member 2 which is attached to handle 3. The absorbent member 2 is preferably a nonwoven fabric containing as constituents anionic and cationic surfactants previously milled into said liquid absorbent member 2 at the manufacturing stage. The two surfactants are in different areas of the fabric so they are in a nonreactive state. The cationic surfactant is a quaternary ammonium salt; and the anionic surfactant is sulfosuccinic acid, ester with ethoxylated lauryl alcohol, disodium salt. These are the preferred surfactants for practicing the invention. The liquid absorbent member 2 can additionally contain active ingredients such as povidone-iodine.

Figure 2:
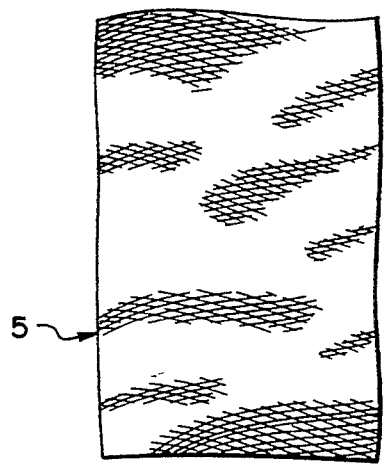
FIG. 2 is an elevational view of flat liquid absorbent fabric in accordance with the present invention.

FIG. 2 shows a device 5 which is a flat porous liquid absorbent fabric containing anionic and cationic surfactants which occupy different areas of the fabric.

In use, when either of the devices 1 and 5 is saturated with an aqueous solution, the surface active properties of the solution are considerably enhanced. When the devices 1 and 5 of FIGS. 1 and 2 are exposed to an aqueous solution having cleaning, disinfecting and sterilizing properties their antimicrobial properties are dramatically and significantly enhanced. The significant surface active activity achieved by anionic and cationic surfactants in aqueous solution makes this invention extremely useful for enhancing aqueous solutions of germicides employed for decontaminating inanimate objects. This invention, moreover, can be extremely useful in enhancing antiseptics used for application to animate surfaces, including mouth washes, toothpaste, and other household products having an aqueous medium.

The preferred germicides are glutaraldehyde, i.e. saturated dialdehydes having from 2 to 6 carbon atoms, in aqueous solution having a concentration of about 0.1 to 2.0% by weight. The solutions may be neutral, acidic potentiated, or alkaline with buffer. The preferred ph is about 1 to 7. A ph of 7 is attained by the addition of an alkaline salt.

A preferred cationic surfactant is bis (2 hydroxyethyl) cocoamine, a quaternary ammonium salt, which constitutes about 0.01 to 2% by weight of the sporicidal composition. The invention may also be practiced with other germicides such as quaternary ammonium compounds, phenols, iodophores, chlorine compounds, alcohol compounds, and hydrogen peroxide.

An alcohol compound according to the invention may include a saturated dialdehyde having from 2 to 6 carbon atoms, about 0.01 to 2% of a cationic surfactant about 0.01 to 2% of an anionic surfactant, and a sufficient quantity of a lower alkanol to make a final alcoholic concentration of about 60 to 70%.

A preferred anionic surfactant is sulfosuccinic acid, ester with ethoxylated lauryl alcohol, disodium salt in a concentration of about 0.1 to 2% by weight of the sporicidal composition.

Carriers for the constituents in a dry form may be powders, tablets, porous members, woven and nonwoven fabrics, nonporous substrates, and plastics such as polyethylene into which the surfactants and other constituents have been milled. The cationic and anionic surfactants are a nonreactive state because they occupy different areas of the carrier. Various carriers such as water and alcohol may be used when the constituents are in solution.

Additional uses of devices 1 and 5 are in the health field where they are components in sponges, dressings, wipes, bandages, and incontinence products, to mention a few.

The device 5 of FIG. 2 can be used in an aerosol spray for surface and space disinfection. Further, it can be an important component in inhalation therapy. In use the device 5 of FIG. 2 can be used as a liner in a container that, when exposed to an aqueous solution of mouthwash, toothpaste, antiseptic or a disinfectant, the respective maximum cleaning and antibacterial effects are enhanced tremendously. The device 5 can also be used as a liner material for a tray for the application of gels and other antimicrobial products to the oral cavity.

Additionally, the device 5 can be tightly wrapped around objects such as medical or dental instruments. The fabric is impregnated with a germicidal solution, and held in an envelope or other hemetically sealed enclosure until sterilization occurs. Sterilization is assisted because the wetted fabric clings to the object, and because the enclosure retains vapors of the solution to promote the exposure of the object to the vapors.

Figure 3:
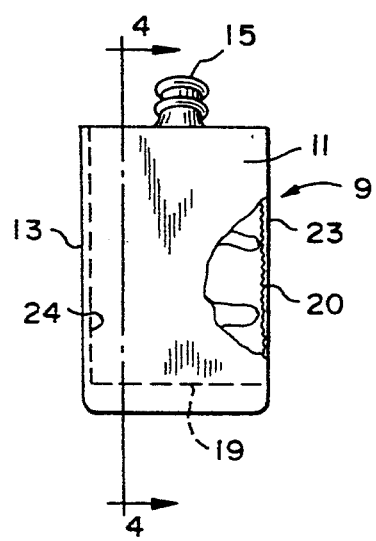
FIG. 3 is an elevational view of an envelope and related components in accordance with the present invention.

There is shown in FIG. 3 a device 9 which includes an envelope 11 which comprises a flaccid, liquid/gas impervious material, thereby preventing the escape of liquids and gases from it. The material is deformable or crushable about an instrument or object which is placed within it, so as to conform substantially to the external shape of the object. A suitable material for envelope 11 is polyethylene, which is heat sealable. Another suitable material is a lamination of flexible sheet material. Within chamber 13 is an absorbent liner 20, which preferably is a nonwoven fabric. The liner 20 is bonded to envelope 11 on its interior walls at 21 and 22 spaced inwardly of and near the opening 19. The liner material 20 contains, as constituents, anionic and cationic surfactants which have been milled into said liner at the manufacturing stage. The opening 19 is sealable with a tie cord, heat seal, adhesive flap, or by other suitable means. There is positioned at the closed end of envelope 11 a valve 15 which is connectable to a vacuum source to achieve vacuum in chamber 13.

Figure 4:
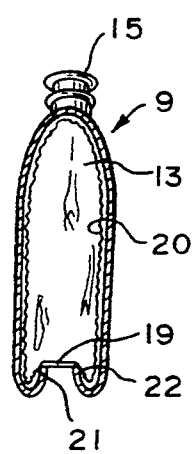
FIG. 4 is a cross-sectional view taken on the line 4—4 of FIG. 3.

Referring now to FIG. 4, a view taken on 4—4 FIG. 3, there is shown device 9 with opening 14a which is a gap in the heat seal line 14, providing communication between chamber 13 and valve 15. This makes it possible to achieve vacuum and to introduce fluids into the chamber 13 by way of valve 15.

In use, an object having irregular surfaces and internal recesses and cavities, such as medical endoscopes and dental handpieces, is placed into chamber 13 through opening 19. The opening 19 is sealed hermetically. A vacuum is drawn through valve 15, thereby creating subatmospheric pressure in chamber 13. A germicide, preferably a glutaraldehyde, is introduced into chamber 13 through valve 15 in a quantity sufficient to permeate and to saturate liner 20. The saturated liner 20 clings and conforms to the exterior shape of the object contained therein. The surfactants contained as constituents within said liner 20 are released to interact with aqueous solution of glutaraldehyde, thereby reducing its surface tension dramatically and significantly to permit rapid destruction of *Clostridium sporogenes* and *Bacillus subtilis* inoculated on suture loops within 5–10 minutes at 25° C. The sterilization process is further enhanced by subjecting it to ultrasonic waves if desired. The use of vacuum is important in this instance to assure that the sporicidal liquid is exposed to all surfaces of the object contained in chamber 13. When the contaminated object is devoid of irregular and internal surfaces, the use of vacuum is not needed. The significance of this system is the discovery of the potent surface active properties of an anionic and a cationic surfactant when employed together in aqueous solution; and, moreover, the innovative and unique method of positioning these surfactants in a liquid absorbent material which is subsequently exposed to an aqueous solution.

In use, the device 9 of FIGS. 3 and 4 requires the following steps:

a contaminated object is placed is chamber 13 through opening 19;

the opening 19 is sealed;

a vacuum is drawn in chamber 13 through valve 15;

the disinfecting solution is introduced into chamber 13 through valve 15;

sufficient contact time is permitted to allow for disinfecting the objects; and the object is removed from chamber 13 through opening 19 and rinsed prior to patient use.

In instances where vacuum is omitted, the contaminated object is placed in chamber 13, the disinfecting solution is introduced through opening 19, and the latter is sealed. Sufficient time is permitted for disinfecting the object. The latter is removed and rinsed prior to patient use.

Figure 5:
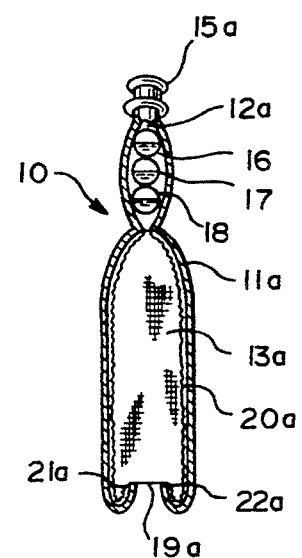
FIG. 5 is a cross-sectional view of an envelope of a further embodiment of the invention.

Referring now to FIG. 5, a device 10 is shown which differs from device 9 in FIG. 3 and FIG. 4 in that there are two chambers, 12a and 13a. Chamber 12a has crushable capsules for containing the anionic and cationic surfactants and other enhancers or buffers where desired. The envelope 11 is divided into a first chamber 12a, and a second chamber 13a. The division of the envelope 11 is by a heat seal 14a which extends partially across the width of envelope 11, there being a gap in the heat seal 14a so as to provide communication between the chamber 12a and 13a.

In its first chamber, 12a, there may be seen three (or more if needed) crushable capsules. 16, 17, and 18, which contain anionic and cationic surfactants in separate capsules. The anionic and cationic surfactants are in a nonreactive state because they are held in separate capsules. Other capsules may contain a buffer or an active ingredient (glutaraldehyde) if so desired; these materials being provided in appropriate quantity relationships in the respective capsules. Within the second chamber 13a is a liner 20a which conforms to the specifications and arrangement of the liner material 20 in device 9 of FIGS. 3 and 4. FIG. 5 reveals a communication between chamber 12a and valve 15a by means of a gap in heat seal 17. In use, the device 10 of FIG. 5 requires the following steps:

the placing of contaminated object into absorbent liner chamber 13a through opening 19a;

the sealing of opening 19a hermetically by suitable means;

drawing vacuum in the two chambers 12a and 13a through valve 15;

crushing the capsules in the unlined chamber 12a;

leaving contaminated object in device 10 for period sufficient for sterilization;

removing object from chamber through opening 19a, and rinsing object prior to patient use.

The embodiments of the invention disclosed in FIGS. 3–5 are extremely effective for cleaning, disinfecting, and sterilizing in liquid phase a large number of objects which are heat sensitive and for whatever reasons, are unavailable to the traditional forms of disinfecting. This is particularly true of instruments and equipment such as medical endoscopes and dental handpieces having irregular surfaces and internal recesses. Such objects require long contact periods for total destruction in aqueous solution of glutaraldehyde (6 ¾ to 10 hours). In this system, the synergistically effectiveness produced by superior surface active properties, vapors, and vacuum in aqueous solutions of glutaraldehyde destroy *Clostridium sporogenes* and *Bacillus subtilis* within 5–10 minutes.

Referring now to FIG. 6, there is shown the device 10 in use and in position on a dental instrument, specifically a dental handpiece H. The entry provided by the cuffs 21a and 22a and the lower portions of the liner 20a will have been opened and the device 10 moved downwardly over the dental handpiece H. The readily manually crushable capsules 16, 17 and 18 will then have been crushed, the fragments being indicated by the dashed lines in the first chamber 12a in FIG. 3. The crushing of the capsules 16, 17 and 18 has released the cold disinfection solution, its surfactants and its buffer or activator, and the activated solution will have passed from the chamber 12a into the chamber 13a, and permeated the liner 20. The device 10 will then have been sealed and secured to the handpiece H by a tie device 25. Then the device 10 will have been deformed or crushed so as to substantially conform to and engage the entire outer surface of the handpiece H. In this way, the cold disinfection solution is and will remain in contact with substantially the entire outer surface of the handpiece H for the requisite time for this disinfection and for sterilization, where desired. In lieu of a handpiece or other instrument, a toothbrush with toothpaste applied to its fibers can be placed into device 10 of FIG. 6 whereby the liner is saturated by the toothpaste and is enhanced in its cleaning properties by the surfactants in said liner.

The dental handpiece H is illustrative of an instrument which is desirably disinfected and sterilized, but is not amenable to immersion. Other dental or medical instruments may be utilized with the herein disclosed devices, as will be readily understood.

Whatever the instrument, and its exterior shape, due to the bonding or adhering of the liner 20a to the envelope 11a in the manner hereinabove disclosed, the entry of the instrument into the second chamber 13a will not dislodge the liner, and neither will the withdrawal of the instrument from the device 10 dislodge the liner.

In FIG. 7, there is shown an alternate embodiment, the device 40 shown therein comprising an envelope 41 defining a single chamber without means for achieving vacuum and having therein an absorbent liner 42 which is bonded to the envelope 41 along an upper line 42a, a lateral edge 42b and an edge opposite to the edger 42b which is not shown in FIGS. 3–6. There is also a bonding of the liner 42 along a pair of lower lines 42c and 42d which extend generally parallel to the lower edges 41a and 41b at the lower end of the envelope 41. The lower portions of the two walls of the liner 42 and the lower portions of the walls forming the envelope 41 provide, in registry, an entry into the device 40. The lower edge of the liner 42 does not extend downwardly beyond the lines 42c and 42d, and therefore below these edges there is provided on the envelope 41 a sealing zone at the entry, which may be provided by the material of which envelope 41 is made, or by some additional material applied to the inner lips of the lower portions of the walls of the envelope 41, such material being a releasable sealant, and providing for hermetic sealing of the interior of the envelope 41. In this embodiment, the cold disinfectant solution has been provided within the device 40, so as to permeate the liner 42, after which the device 40 is sealed.

In use, the device 40, sealed as indicated and with the absorbent liner 42 permeated with the noted cold disinfection solution, is opened at the seal to provide an entry. Objects to be disinfected are inserted within the device 40 or the device 40 is placed over such an object, and is then deformed, as necessary, so that the entire outer surface of the object is engaged by the permeated or saturated liner 42.

In FIG. 8, there is shown a device 50 in accordance with the present invention and comprising an envelope 51 of the same material as the envelope 11, being divided into an upper chamber 52 and a lower chamber 53 by a heat seal 55 extending partially across the envelope. Within the first chamber 52 are three capsules 16b, 17b and 18b which contain the same materials, and have the same attributes as the capsules 16, 17 and 18 of the embodiment shown in FIG. 5. In the embodiment of FIG. 7, the second chamber 53 is not provided with a liner, but its lower end has a seal zone indicated generally by the reference numeral 54, provided at the lower ends of the walls forming the second chamber 53, and being positioned so as to seal the entry into the second chamber 53.

In use, an instrument or other object is inserted into the chamber 53, and utilizing the sealing zones 54 and the adhesive qualities thereof, sealing is effected about the instrument or object, or sealing is effected between the two zones 54 if the instrument is of such size as to be completely housed or contained within the chamber 53. Such an instrument may be, for example, a thermometer, a toothbrush or some other instrument which would not be harmed by immersion. Thereafter, the crushable capsules are broken, and the cold disinfection solution is activated and caused to flow into the chamber 53 where it contacts and disinfects the object, or sterilizes the object, if contact occurs for a sufficient length of time.

Referring now to FIG. 9, there is shown device 80, which is a container for holding fluid. There is provided another wall 83, and an entry 89 into an inner chamber 85 of device 80. There is shown in chamber 85 a liquid absorbent liner 82 which is preferably a nonwoven fabric, and contains as constituents anionic and cationic surfactants. In use, when an aqueous solution is exposed to the absorbent liner 82, its surface active properties are increased substantially. Aqueous solutions that could benefit from this embodiment of the invention are those having cleaning, disinfecting, and sterilization properties, including mouth washes, gargles and toothpaste.

There is shown in FIG. 10 a device 90 which is a tray having an outer body 92 having a handle 93. The inner body 94 is provided with an absorbent liner material which contains as constituents anionic and cationic surfactants. In use, the device 90 is ideal for applying gels, creams or other beneficial substances to the oral cavity, including the teeth. The antimicrobial action of such substances is substantially enhanced by their decreased surface tension.

In lieu of the surfactants in crushable capsules as shown in device 50 of FIG. 8, or being the constituents of the absorbent material of devices 80 and 90 of FIG. 9 and 10, the constituents could be positioned on suitable substrates and the latter devices; or the surfactants could be milled into the polyethylene walls of device 50 of FIG. 8. This is possible according to the current state-of-the-art. The devices 80 and 90 of FIG. 9 could be made from materials such as polystyrene, polystyrofoam, or polyethylene, where the surfactants are contained therein, and or released as indirect additives when exposed to aqueous solutions of various kinds, whereby surface tension is reduced dramatically.

A nonwoven fabric is broadly defined as sheet or web structures made by bonding or entangling fibers or filaments by chemical, thermal or mechanical means. They are not made by the traditional processes of weaving or knitting. Generally, nonwoven fabrics contain three systems in their manufacturing processes. These include a fiber system, binder system and finish system. The fiber system refers to the fibers used in the nonwoven. The binder systems refers to the means of bonding the fiber together in a web-like structure. The finish system refers to the properties imparted to the nonwoven such as appearance, durability, strength, softness—and importantly—wickering and wetting properties, etc.

Important to accomplishing these manufacturing systems in nonwoven production calls for the use of an array of chemical compounds. The chemical compounds include, but are not limited to, polymer types such as acrylics, styrene-butadene, vinylacetate acrylics, urea and melamine formaldehyde. Chemicals used in the finishes are formulated from mixtures of lubricants, antistatic agents and compounds chosen from those used as surfactants. Some material fibers used in nonwoven production being negatively charged are strongly attracted to cationic surfactants in aqueous solution. This is the phenomenon suspected in providing such dramatic surface active activity in aqueous solutions supplemented with cleaning, disinfecting and sterilizing compositions. By milling in a cationic and an anionic (in dry state) surfactant in the nonwoven when exposed to an aqueous medium, the surfactants considerably lower surface tension. The nonwoven fabric of choice for use in this invention is one having the following specifications:

| | |
|---|---|
| Binder Type: | Acrylic |
| Fiber Content: | 100% Rayon |
| Grade Number: | 20070 stage.22 |
| Weight: | 0.7 oz/yd |
| Furnish: | Rayon |
| Manufacturer: | International Paper Company 77 West 45th Street New York, NY 10036 |

There are countless numbers of chemical compounds used as surface active agents. And the inventor has many suitable surfactants to choose from. For example, anionic surfactants, those bearing a negative charge, are derived from materials that are alkali metal salts of fatty acid and anions of long chain surfactants, sulfates and phosphates; cationic surfactants, those bearing a positive charge, are made from amine salts, quaternary ammonium or pyridinium compounds.

The surfactants of choice to enhance the acid glutaraldehydes are selected from an extensive array of chemicals representing cationic and other surface active agents. As previously stated, this system can accommodate surfactants having opposing electrical charges. The preferred choice of a cationic surfactant is an ethoxylated aliphatic amine. The brand favored is Ethomeen C12, a product of Akzo Chemie Americo Organic Chemicals (300 S. Riverside Plaza, Chicago, Ill. 60606). Its formulation structure is represented as:

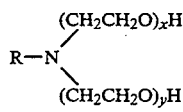

The anionic surfactant of choice for use in this system is sulfosuccinic acid, ester with ethoxylated lauryl alcohol, disodium salt. The brand is Elfanol 616, a product of the company listed above. The formula is represented as:

$$C_{12-14}(CH_2CH_2O)_3\text{-}C_4H_3O_4S\text{-}Na_2$$

Additional cationic surfactants of choice for use in this invention are acetylpyridinium chloride, and benzalkonium chloride.

The number of germicides that can find use in this invention are both extensive and varied. They include glutaraldehyde, phenols and phenol derivatives, hexochlorphene, alcohols, iodine, iodine preparations, iodophors, chlorine compounds, quaternary ammonium compounds, formaldehyde, hydrogen peroxide, and many others. The germicide of choice for application to animate surfaces and objects is povidone-iodine.

The germicide of choice for application to inanimate surfaces and objects is Ucricide ® (Union Carbide) an acid glutaraldehyde. This invention can accommodate an alkaline glutaraldehyde by employing buffers in crushable capsules. It is significant that commercially available glutaraldehyde products such as Sporicidal ®, Cidex Plus ®, Coldcide ®, and Banicide ® can be utilized in this invention without altering their respective formulations. The contact time for destroying highly resistant spores in this invention is 5-10 minutes versus 6 ¾-10 hours in the conventional immersion system. Also, the time required for destruction of highly resistant spores is reduced from 26 hours to 3 hours employing Betadine ® (povidone-iodine). The reduction of contact time required for disinfection/sterilization has been observed when using germicides such as isopropyl alcohol, hydrogen peroxide (3%), hypochlorite (5.25%) and melamine formaldehyde (0.05%).

There have been provided devices for utilization with cold disinfection solution for engaging the entire outer surface and internal recesses of an object to be disinfected or sterilized. Each of the devices is readily fabricated, and is inexpensive, providing disinfection and/or sterilization, without immersion where immersion is undesirable.

REFERENCES

The following publications are incorporated herein by reference:

*Nonwoven Handbook.* Association of the Nonwoven Fabrics Industry.

*Surfactants And Interfacial Phenomena.* 2nd Edition. Milton J. Rosen. pp 75-80; pp. 240-252.

*Antiseptics, Disinfectants, Fungicides And Sterilization.* 2nd Edition. G. F. Reddish. pp. 203-267; pp. 330-331.

EXAMPLES

The following examples to illustrate the invention. They are given primarily for the purpose of illustration and should not be construed as limiting the invention to the details given.

Purpose

To determine the minimum exposure conditions required for the test system to exhibit sporicidal activity against *Bacillus subtilis* ATCC #19659, and *Clostridium sporogenes* ATCC 3584.

Test Method

The test method used was a modification of the sporicidal method, Chapter 4. Disinfectant paragraphs 4,033–4,085, *Official Methods Of Analysis of the Association of Official Analytical Chemists.*

The test germicides used were Uricide ® reduced to a acid glutaraldehyde, Banicide ®, a 2% acid glutaraldehyde, and Cidex (regular), an alkaline glutaraldehyde.

| The nonwoven material used was: | |
|---|---|
| Binder Type: | Acrylic |
| Fiber Content: | 100% Rayon |
| Grade Number: | 20070 stage.22 |
| Weight: | 0.7 oz/yd |
| Furnish: | Rayon |
| Manufacturer: | International Paper Company 77 West 45th Street New York, NY 10036 |

The anionic surfactant used was a sodium lauryl sulfate compound which was a constituent of the above nonwoven product. The cationic surfactants used were an ethoxylated aliphatic amine compound, and benzalkonium chloride.

A modification of the method involved using the pouches as containers for the germicide rather than the 25×150 mm medication tubes specified in the method. The following tests were performed by placing test sutures in pouches of the type shown in FIGS. 3 and 4, wherein the openings 19 were sealed by adhesive tape.

The amount of germicide used in each pouch was 12 ml.

All tests were conducted at 25° C.

All culture in pouches were incubated for 21 days after which they were heat shocked.

EXAMPLE I

Forty (40) nylon sutures were contaminated with a 72 hour culture of *Clostridium sporogenes* ATCC #3584. The suture loops were exposed to a 2% acid glutaraldehyde solution (Banicide ®) supplemented with anionic and cationic surfactants.

Results

| Positive control ... growth in 24 hours 2/2 | | |
|---|---|---|
| Organism | Carrier | Contact Time |
| *Clostridium sporogenes* | Sutures | 10 minutes 0/40 |

Discussion

The supplemented 2% acid glutaraldehyde solution proved to be sporicidal within ten (10) minutes when supplemented with anionic and cationic surfactants. These findings are outstanding considering that 6¾ hours to 10 hours are required to inactivate *Clostridium sporogenes* in the conventional immersion system using Banicide ®.

The acid resistance test was 10 minutes.

EXAMPLE II

Because of the outstanding results obtained in Example I, the test was repeated reducing the contact time to five (5) minutes.

Results

| Positive control . . . growth in 24 hours 2/2 | | |
|---|---|---|
| Organism | Carrier | Contact Time |
| Clostridium sporogenes | Sutures | 5 minutes 1/20 |

Discussion

Albeit one failure, this test once again demonstrates the significant lowering of surface tension when employing anionic and cationic surfactants as supplements to the acid glutaraldehyde.

The acid resistance test was 20 minutes.

EXAMPLE III

This test was performed to determine the efficacy of the system when employing spores of Bacillus subtilis ATCC 19659, and an acid glutaraldehyde.

Results

| Positive control . . . growth in 24 hours 2/2 | | |
|---|---|---|
| Organism | Carrier | Contact Time |
| Bacillus subtilis | Sutures | 5 minutes 0/15 |

Discussion

Again the supplemented glutaraldehyde demonstrates the powerful surface active properties of anionic and cationic surfactants in aqueous solutions of glutaraldehyde.

The acid resistance test was 15 minutes.

EXAMPLE IV

This test was performed to determine the efficacy of vacuum on the system, employing an unsupplemented 2% acid glutaraldehyde (Uricide ®).

Results

| Positive control . . . growth in 24 hours 2/2 | | | | | | |
|---|---|---|---|---|---|---|
| Organism | Carrier | | Contact Time | | | |
| Clostridium sporogenes 25 | Sutures 3/3 | 5 min 3/3 | 10 3/3 | 15 3/3 | 20 0/3 | |

*When Banicide ® was used, the spores were inactivated within 20 minutes.

Discussion

The effect of vacuum in this system is highly effective in reducing contact time when highly resistant spores are exposed to glutaraldehyde. The use of vacuum employing a supplemented 2% acid glutaraldehyde did not reduce contact time from 5–10 minutes as in Examples I–III. This further attests to the efficacy of the anionic and cationic to significantly lower surface tension.

EXAMPLE V

This in-use test was performed to determine the efficacy of a supplemented acid glutaraldehyde (anionic and cationic surfactants) enhanced with vacuum and ultrasonic in inactivating handpieces (contra-angle) contaminated with Clostridium sporogenes.

Results

| Positive control . . . growth in 24 hours 2/2 | | |
|---|---|---|
| Organism | Carrier | Contact Time |
| Clostridium sporogenes | Sutures | 10 minutes 0/4 |

Discussion

This test was highly significant in that the handpiece with its gross irregular surfaces and internal cavities represent one of the most difficult instruments to sterilize. It is more difficult to sterilize than the medical endoscope, which other than ethylene oxide sterilization, must be content with disinfection in aqueous solutions of glutaraldehyde.

The acid resistance test was 10 minutes.

EXAMPLE VI

This test was performed to determine the efficacy of an antiseptic to inactivate highly resistant spores when supplemented with anionic and cationic surfactants. The antiseptic employed was Betadine ® (povidone-iodine).

Results

| Positive control . . . growth in 24 hours 2/2 | | | | |
|---|---|---|---|---|
| Organism | Carrier | | Contact Time | |
| Bacillus subtilis | Sutures | 2 hrs 12/12 | 2-1/2 8/8 | 3 0/8 |

Discussion

Germicides which can be applied to animate surfaces and objects are extremely important in preventing and controlling infections. The unsupplemented Betadine ® requires 26 hours to inactivate the above spore employing the conventional immersion system. Any antiseptic so supplemented to enhance its sporicidal properties is extremely important in treating wound sites and other areas of the body. This enhanced activity, when exposed to this system, has been observed in hydrogen peroxide (3%), and in isopropyl alcohol (70%).

The acid resistance test was 15 minutes.

EXAMPLE VII

Soft contact lenses were contaminated with Aspergillus fumigatus exposed to hydrogen peroxide (3%). The lenses were tested to determine the contact time required to inactivate this organism on the contact lenses when a supplemented hydrogen peroxide (3%) solution was employed.

Materials
1. Contact lenses—Softmate II (Barnes Hind, Inc.,)
2. Hydrogen peroxide (3%) (Parke Davis)
3. Aspergillus fumigatus ATCC 16903
4. Catalase Results

| Positive control . . . growth within 24 hours 2/2 | | |
|---|---|---|
| Organism | Carrier | Contact Time |
| Aspergillus fumigatus | Contact Lenses | 5 mins 0-/5 (after 7 days) |

Discussion

The ability of 3% hydrogen peroxide supplemented with anionic and cationic surfactants to inhibit this fungus within 5 minutes is significant; however, it is felt by the inventor that this contact time can be further reduced to inhibit *Aspergillus fumigatus*. The latter requires forty-five minutes or more for inactivation with hydrogen peroxide 3% in the regular immersion system.

EXAMPLE VIII

The purpose of this test was to determine the minimum exposure conditions required for the test system to inactivate *Bacillus subtilis* ATCC 19659 with an unsupplemented alkaline 3.2% glutaraldehyde within the closed system device. The sporicidal activity exhibited was enhanced by the vapor omitted from the 3.2% alkaline glutaraldehyde and trapped within the closed system device.

Results

| Positive control . . . growth within 24 hours 2/2 | | | |
|---|---|---|---|
| Organism | Carrier | Contact Time | |
| *Bacillus subtilis* | Cylinders | 10 mins 0/10 | 15 mins 0/10 |

Discussion

This test was significant in that the 20 contaminated cylinders employed were negative after contact periods of 10 mins and 15 mins. at 20° C. (instead of 25° C.). It demonstrates the value of the closed system synergistically utilizing the glutaraldehyde solution and its emitted vapors. In the regular immersion system, this organism requires about 3 hours at room temperature for inactivation by 3.2% alkaline glutaraldehyde.

This acid resistance test was 3 minutes.

It will be obvious to those skilled in the art that various changes may be made without departing from the spirit of the invention, and therefore the invention is not limited to what is shown in the drawings and described in the specifications but only as indicated in the amended claims.

EXAMPLE IX

The purpose of this test was to determine the minimum exposure condition required for the test system to inactivate *Clostridium sporogenes*, employing a 2% alkaline glutaraldehyde.

| Positive control . . . growth within 24 hours 2/2 | | |
|---|---|---|
| Organism | Carrier | Contact Time |
| *Clostridium sporogenes* | Sutures | 10 mins 7/96 |

Discussion

This test was significant in that the pleasing results observed with the use of an acid glutaraldehyde was shown to be just as effective when using an alkaline glutaraldehyde. This demonstrates the efficacy of the system to handle various forms of glutaraldehyde and other germicides.

The acid resistance test was 20 mins.

I claim:

1. A rapid sporicidal composition comprising
a germicide,
an anionic surfactant, and
a cationic surfactant.

2. A sporicidal composition according to claim 1, in which a porous body contains the anionic surfactant.

3. A sporicidal composition according to claim 1, in which a porous body contains the cationic surfactant.

4. A sporicidal composition according to claim 1, wherein the composition includes about 0.01 to 2% by weight of said cationic surfactant, and about 0.01 to 2% by weight of said anionic surfactant.

5. A sporicidal composition according to claim 1, wherein the cationic surfactant is a bis (2 hydroxyethyl) cocoamine.

6. A sporicidal composition according to claim 1, wherein the anionic surfactant is sulfosuccinic acid, ester with ethoxylated lauryl alcohol, disodium salt.

7. A sporicidal composition according to claim 1, wherein the cationic surfactant is a quaternary ammonium salt.

8. A sporicidal composition according to claim 1, wherein the germicide is selected from the group consisting of quaternary ammonium compounds, phenols, iodophores, acidic potentiated glutaraldehydes, neutral glutaraldehydes, alkaline glutaraldehydes with buffer, chlorine compounds, alcohol compounds, and hydrogen peroxide.

9. A sporicidal composition according to claim 1, wherein the germicide includes a glutaraldehyde comprising a saturated dialdehyde having from 2 to 6 carbon atoms.

10. A sporicidal composition according to claim 9, wherein the germicide is a solution containing about 0.1 to 2% by weight of said glutaraldehyde, about 0.01 to 2% by weight a cationic surfactant, and about 0.01 to 2% by weight of an anionic surfactant.

11. A sporicidal composition according to claim 10, wherein the cationic surfactant is bis (2 hydroxyethyl) cocoamine, and the anionic surfactant is sulfosuccinic acid, ester with ethoxylated lauryl alcohol, disodium salt.

12. A sporicidal composition according to claim 9, including about 0.01 to 2% by weight of a cationic surfactant, about 0.01 to 2% by weight of an anionic surfactant, and a sufficient quantity of a lower alkanol to make a final alcoholic concentration from about 60 to 70%.

13. A sporicidal composition according to claim 11, containing from about 0.1 to 2% by weight of glutaraldehyde which is the germicide, about 0.01 to 2% by weight of said anionic surfactant, about 0.01 to 2% by weight of said cationic surfactant, and an alkaline salt providing a ph of about 7 to 8.

14. A sporicidal composition according to claim 1, containing from about 0.1 to 2% by weight of glutaraldehyde Which is the germicide, about 0.01 to 2% by weight of said anionic surfactant, and about 0.01 to 2% by weight of said cationic surfactant, said composition having a ph of 1 to 7.

15. A method of sterilizing an object by exposing the object to the composition of claim 1 for a period of time sufficient to achieve sterilization.

16. A method according to claim 15, including the preliminary steps of providing an envelope which is substantially impervious to gas and liquid, said envelope containing a member which includes an anionic surfactant, and introducing into said envelope a germicidal solution which contains said cationic surfactant.

17. A method according to claim 15, wherein said member is an absorbent liner located within said envelope.

18. A method according to claim 15, including the step of removing air from said envelope.

19. A method according to claim 15, including the step of providing a vacuum within said envelope.

20. A method according to claim 15, including the step of subjecting the object to ultrasonic waves.

* * * * *